US006335383B1

(12) United States Patent
Scopelianos et al.

(10) Patent No.: US 6,335,383 B1
(45) Date of Patent: *Jan. 1, 2002

(54) MICRODISPERSIONS FOR COATING SURGICAL DEVICES

(75) Inventors: Angelo G. Scopelianos, Whitehouse Station; Steven C. Arnold, Sparta; Rao S. Bezwada, Whitehouse Station; Mark B. Roller, North Brunswick; Shawn T. Huxel, Lakehurst; Robert J. Tannhauser, Bridgewater, all of NJ (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/806,120

(22) Filed: Mar. 7, 1996

Related U.S. Application Data

(63) Continuation-in-part of application No. 08/324,543, filed on Oct. 18, 1994, now Pat. No. 5,599,852.

(51) Int. Cl.⁷ .............................................. A61B 17/04
(52) U.S. Cl. ........................ 523/105; 606/228; 606/230; 606/231
(58) Field of Search ......................................... 523/105

(56) References Cited

U.S. PATENT DOCUMENTS

| | | | |
|---|---|---|---|
| 4,595,713 A | 6/1986 | St. John | 523/105 |
| 4,643,734 A * | 2/1987 | Lin | 623/16 |
| 4,664,655 A | 5/1987 | Orentreich et al. | 604/232 |
| 4,705,820 A * | 11/1987 | Wang | 524/381 |
| 4,758,234 A | 7/1988 | Orentreich et al. | 604/232 |
| 4,803,075 A | 2/1989 | Wallace et al. | 424/423 |
| 4,938,763 A | 7/1990 | Dunn et al. | 604/891.1 |
| 5,204,382 A | 4/1993 | Wallace et al. | 523/115 |
| 5,278,201 A | 1/1994 | Dunn et al. | 523/113 |
| 5,278,202 A | 1/1994 | Dunn et al. | 523/113 |
| 5,321,113 A | 6/1994 | Cooper et al. | 528/176 |
| 5,340,849 A | 8/1994 | Dunn et al. | 523/113 |
| 5,366,756 A * | 11/1994 | Chesterfield | 427/2.26 |
| 5,458,099 A | 10/1995 | Koller et al. | 123/193 |
| 5,468,253 A | 11/1995 | Bezwada et al. | 606/230 |

FOREIGN PATENT DOCUMENTS

| | | | | |
|---|---|---|---|---|
| DE | 42 35 312.2 | | 4/1993 | C08L/67/04 |
| EP | 0 608 139 A1 | | 1/1994 | A61L/17/00 |
| EP | 0 635 531 A2 | | 7/1994 | C08G/63/08 |
| WO | WO 93/15721 | | 8/1993 | A61K/9/14 |
| WO | WO 94/02184 | | 3/1994 | A61L/27/00 |

OTHER PUBLICATIONS

J. of Urology, vol. 151, May 1994, No. 5 Injectable Teflon Paste for Female Stress Incontinence: long term Follow–up and Results; J. F. Buckley, et al.

Neurourology and Urodynamics 12:131–137 (1993) Complications of Teflon Injection for Stress Urinary Incontinence Pentti, et al.; 1993 Wiley–Liss, inc.

J. of Urology vol. 142, 821–822, Pulmonary Migration Following Periurethral Polytetrafluoroethylene Injection for Urinary Incontinence H. Claes, et al.

Plastic & Reconstructive Surgery –Apr. 1991, vol. 87, 693–702, Bioplastique: A New Textured Copolymer Microparticle Promises Permanence in Soft–Tissue Augmentation Robert A. Ersek, M.D., et al.

J. of Urology vol. 148, 1797–1800, Dec. '92, Early Experimence with Intrauuethral Collagen Injections for urinary Incontinence Sender Herschorn, et al.

JAMA Jun. 22/29, 1984–vol. 251, No. 24 3277–3281, Clinical Investigation: Migration and Granulomatous Reactino After Periurethral Injection of Polytef (Teflone)Anthont A. Malizia, Jr. M.D., et al.

J. of Endourology vol. 6, No. 3, '92, 275–277, Endourologic Control of Incontinence with GAX Collagne: The LSU Experinece Rodney A. Appell, M.D., et al.

J. American Acad. Dermatol. Dermatologic Surgery; No. 5, Nov. 1989, 992–998, Dermal Implants: Safety of Products Injected for Soft Tissue Augmentation David P. Clark, et al.

Dermatologic Clinics, vol. 11 –No. 2, Apr. '93, 361–367, Dermal Filler Materials Melvin L. Elson, M.D.

J. Dermatol. Surg. Oncol. 14:7 Jul. 1988, 66–75, Comparison of Injectable Silicone Versus Collagen for Soft Tissue Augmentation Kevin A. Shumrick, M.D., et al.

Clinics in Plastic Surgery vol. 18, No. 4, Oct. '91, 829–855, Alloplastic Implants for Men Brian H. Novack, M.D.

Donaldson, Lufkin & Jenrett Research Bulletin, Oct. 6, 1993, 1565–93 Kent Blair.

Aesthetic Plastic Surgery, 16:59–65, 1992, Bioplastique: A New Biphasic Polymer for Minimally Invasive Injection Implantation Robert A. Ersek, M.D., et al.

* cited by examiner

*Primary Examiner*—Paul R. Michl

(57) ABSTRACT

The present invention provides surgical article and suture coated with bioabsorbable microdispersions which contains a fluid carrier that is a liquid polymer and a particular material.

30 Claims, 1 Drawing Sheet

MICRODISPERSIONS FOR COATING SURGICAL DEVICES

FIELD OF THE INVENTION

The present invention is a continuation-in-part of application Ser. No. 08/324,543 filed Oct. 18, 1994, now U.S. Pat. No. 5,599,852, (hereby incorporated by reference). The present invention relates to microdispersions that are suitable for providing bioabsorbable coatings for surgical devices. More specifically, the present invention provides biocompatible, bioabsorbable, copolymer microdispersions that are suitable for coating surgical devices.

BACKGROUND OF THE INVENTION

The repair or augmentation of soft tissue defects or contour abnormalities caused by facial defects, acne, surgical scarring or aging has proven to be very difficult. A number of materials have been used to correct soft tissue defects with varying degrees of success, but currently no material appears to be completely safe and effective. In the past, small amounts of liquid silicone were used to correct minor soft tissue defects where minimal mechanical stress was present at the recipient site. Unfortunately, liquid silicone from these injections appears to migrate to distant body parts and causes a variety of physiological and clinical problems. In response to these problems and the misuse of liquid silicone, the FDA has prohibited the use of liquid silicone in humans.

In the 1970's, reconstituted injectable bovine collagen became available and appeared to be an effective treatment for soft tissue defects. However, over time, the benefits of the collagen treatment have proven to be short-lived; the collagen reabsorbs in two to three months. Additionally, safety measures must be employed with this material to avoid allergic reactions to the bovine proteins in the collagen. To solve these shortcomings, crosslinked collagen has been introduced to extend the effect of treatments to approximately six (6) months. However, allergic reactions still occur with the crosslinked collagen material and frequent readministration of the crosslinked material is still required.

Recently, several authors have described new materials that may be used for soft tissue repair or augmentation such as biocompatible ceramic particles in aqueous gels, thermoplastic materials, thermosetting materials and lactic acid based polymer blends that avoid some of the problems previously experienced with collagen and liquid silicone.

Injectable implants of biocompatible ceramic particles in aqueous gels were first proposed by Wallace et al. in U.S. Pat. No. 5,204,382. The implants consisted of ceramic particles of calcium phosphate from a nonbiological source, mixed with an aqueous gel carrier in a viscous polymer (such as polyethylene glycol, hyaluronic acid, poly (hydroxyethyl methacrylate) and collagen). Although these materials are generally nontoxic, there appears to be risks associated with the use of nonabsorbable particulate materials related to the migration of these particles to distance sites in the body.

Thermoplastic and thermosetting defect fillers were originally described by Dunn et al. in U.S. Pat. Nos. 4,938,763, 5,278,201 and 5,278,202. In these patents, Dunn proposes the use of both a thermoplastic material with a solvent and a thermosetting material with a curing agent to form solid implants in situ. Although the biodegradable materials Dunn suggests for use as thermoplastics appear acceptable, the solvents necessary to dissolve them for injection into tissue appear to be less than acceptable. Additionally, Dunn's thermoplastic and thermosetting materials have limited utility in filling soft tissue because they solidify. Similar commercially available materials exhibit ultimate yield stresses of approximately 10,000 psi; in comparison, human skin exhibits ultimate yield stresses of from 500 to 2,000 psi. Therefore, due to palpability concerns, the thermoplastic and thermosetting materials that Dunn proposed appear to be too hard for use in soft tissue augmentation or repair and especially in dermal augmentation or repair.

Soft tissue repair or augmentation has also been proposed using lactic acid based polymer blends of amorphous oligomers with crystalline oligomers or polymers (Buchholz et al. 4,235,312 A1). Buchholz's blends were developed to provide a pasty to waxy material which could be used as an absorbable implant to replace the brittle copolymers of lactic acid and glycolic acid already described for use as bone waxes. However, these blends do not appear to be suitable for use as injectable soft tissue defect fillers, because they are too viscous to be injected through a needle which significantly limits the utility of these blends. Furthermore, the low molecular weight liquid oligomers described by Buchholz are slightly soluble in body fluids, which means that these oligomers will quickly diffuse out of the site of implantation to other areas of the body.

In view of the deficiencies of the soft tissue augmentation materials previously considered, it is evident that new soft tissue augmentation materials need to be developed. Ideally, any new augmentation material would have several important characteristics not possessed by any one of the previously discussed materials. For example, any new augmentation material should be completely bioabsorbable to avoid the possibility of long term chronic irritation of tissues or migration of nonabsorbable materials over time to different areas of the body. The new augmentation materials should also provide soft tissue augmentation for at least six months to avoid frequent readministration of the augmentation material. Furthermore, new soft tissue augmentation materials should be easy to administer preferably by injection. Finally, the ideal soft tissue augmentation material would have the appropriate degree of pliability for the tissue into which the new material was being implanted to provide life like tissue augmentation. As discussed above, none of the currently available materials have all of these characteristics.

Therefore, it is an object of the present invention to provide a safe, injectable, long lasting, bioabsorbable, soft tissue repair and augmentation material.

SUMMARY OF THE INVENTION

The present invention provides fluid, injectable, bioabsorbable microdispersions suitable for use as a soft tissue repair or augmentation material in animals comprising a fluid carrier that is a liquid polymer selected from the group consisting of liquid polymers of at least two first repeating units and liquid polymers of a plurality of first lactone and second lactone repeating units; wherein the first lactone repeating units are selected from the group consisting of ε-caprolactone repeating units, trimethylene carbonate repeating units, ether lactone repeating units (which for the purpose of this invention shall mean 1,4-dioxepan-2-one and 1,5-dioxepan-2-one) and combinations thereof and the second lactone repeating units are selected from the group consisting of glycolide repeating units, lactide repeating units (which for the purpose of this invention are defined to be L-lactide, D-lactide, or D,L-lactide repeating units), p-dioxanone repeating units and combinations thereof; and a particulate material that is selected from the group consisting of solid homopolymers of poly(ε-caprolactone), solid homopolymers of poly(p-dioxanone), solid homopolymers of poly(trimethylene carbonate), solid copolymers of a plurality of ε-caprolactone repeating units and third lactone repeating units, solid copolymers of a plurality of trimethylene carbonate repeating units and second lactone repeating unit; wherein the third lactone repeating units are selected from the group consisting of glycolide repeating units, lactide repeating units, trimethylene carbonate repeating units, p-dioxanone repeating units, 1,4-dioxepan-2-one repeating units, 1-5-dioxepan-2-one repeating units and combinations thereof.

In another embodiment of the present invention, there is also provided a prefilled pharmaceutical container having a fluid, injectable, bioabsorbable, microdispersion loaded therein, comprising: a) a microdispersion of a fluid carrier that is a liquid polymer selected from the group consisting of liquid polymers of at least two first lactone repeating units and liquid polymers of a plurality of first lactone and second lactone repeating units; wherein the first lactone repeating units are selected from the group consisting of ε-caprolactone repeating units, trimethylene carbonate repeating units, ether lactone repeating units and combinations thereof and the second lactone repeating units are selected from the group consisting of glycolide repeating units, lactide repeating units, p-dioxanone repeating units and combinations thereof; and a particulate material that is selected from the group consisting of solid homopolymers of poly(ε-caprolactone), solid homopolymers of poly(p-dioxanone), solid homopolymers of poly(trimethylene carbonate), solid copolymers of a plurality of ε-caprolactone repeating units and third lactone repeating units, solid copolymers of a plurality of trimethylene carbonate repeating units and second lactone repeating unit; wherein the third lactone repeating units are selected from the group consisting of glycolide repeating units, lactide repeating units, trimethylene carbonate repeating units, p-dioxanone repeating units, 1,4-dioxepan-2-one repeating units, 1-5-dioxepan-2-one repeating units and combinations thereof; and b) a container for storing said microdispersion, said container having a cylindrical storage area and an outlet and an end to said cylindrical storage area, the outlet having a removable sterile seal, the end having a movable sterile seal which may be advanced into said cylindrical storage area.

In yet another embodiment of the present invention, there is also provided a pharmaceutical kit suitable for administering a fluid, injectable, bioabsorbable microdispersion comprising: a) a microdispersion of a fluid carrier that is a liquid polymer selected from the group consisting of liquid polymers of at least two first lactone repeating units and liquid polymers of a plurality of first lactone and second lactone repeating units; wherein the first lactone repeating units are selected from the group consisting of ε-caprolactone repeating units, trimethylene carbonate repeating units, ether lactone repeating units and combinations thereof and the second lactone repeating units are selected from the group consisting of glycolide repeating units, lactide repeating units, p-dioxanone repeating units and combinations thereof; and a particulate material that is selected from the group consisting of solid homopolymers of poly(ε-caprolactone), solid homopolymers of poly(p-dioxanone), solid homopolymers of poly(trimethylene carbonate), solid copolymers of a plurality of ε-caprolactone repeating units and third lactone repeating units, solid copolymers of a plurality of trimethylene carbonate repeating units and second lactone repeating unit; wherein the third lactone repeating units are selected from the group consisting of glycolide repeating units, lactide repeating units, trimethylene carbonate repeating units, p-dioxanone repeating units, 1,4-dioxepan-2-one repeating units, 1-5-dioxepan-2-one repeating units and combinations thereof; and b) a device containing said microdispersion, said device having an outlet for said microdispersion, an ejector for expelling the microdispersion through the outlet and a hollow tubular member fitted to the outlet for administering the microdispersion into a site within the body.

In yet a further embodiment of the present invention there is also provided a surgical article (such as a suture) wherein the outer surface is coated with a microdispersion comprising: a surgical device at least partially coated with a fluid, bioabsorbable microdispersion composed of a fluid carrier that is a liquid polymer selected from the group consisting of liquid polymers of at least two first lactone repeating units and liquid polymers of a plurality of first lactone and second lactone repeating units; wherein the first lactone repeating units are selected from the group consisting of ε-caprolactone repeating units, trimethylene carbonate repeating units, ether lactone repeating units and combinations thereof and the second lactone repeating units are selected from the group consisting of glycolide repeating units, lactide repeating units, p-dioxanone repeating units and combinations thereof; and a particulate material that is selected from the group consisting of solid homopolymers of poly(ε-caprolactone), solid homopolymers of poly(p-dioxanone), solid homopolymers of poly(trimethylene carbonate), solid copolymers of a plurality of ε-caprolactone repeating units and third lactone repeating units, solid copolymers of a plurality of trimethylene carbonate repeating units and second lactone repeating unit; wherein the third lactone repeating units are selected from the group consisting of glycolide repeating units, lactide repeating units, trimethylene carbonate repeating units, p-dioxanone repeating units, 1,4-dioxepan-2-one repeating units, 1-5-dioxepan-2-one repeating units and combinations thereof.

DETAILED DESCRIPTION OF THE INVENTION

Figure 1:
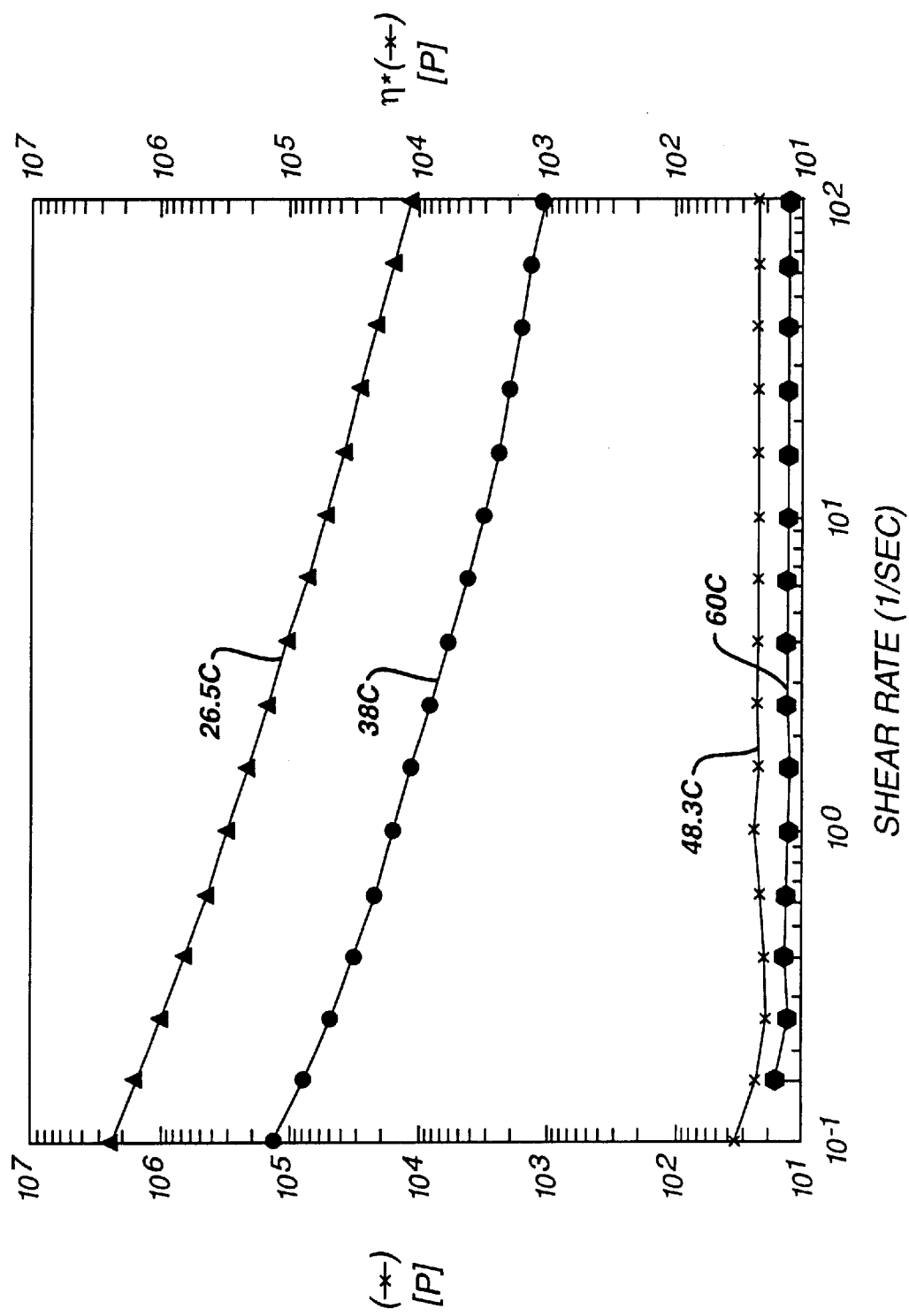
FIG. 1 illustrates the shear thinning nature of the inventive microdispersion at 26.5° C. and 38° C. The data at 48.3° C. and 60° C. demonstrates that when the microdispersion looses it solid phase it becomes a Newtonian fluid.

We have surprisingly discovered that by selecting appropriate combinations of a fluid carrier and a particulate material, both made from bioabsorbable polymers, that shear thinning bioabsorbable microdispersions can be formed. These microdispersions have remarkably low viscosities at high shear rates which enable the material to be injected into soft tissue with a syringe and needle without heating or solvents. Additionally, these microdispersions, unlike materials which harden after implantation, are suitable for restoring dermal tissue with the pliability similar to natural tissue. The microdispersions also, unlike the viscous liquids used in the past, may be formulated to have a yield stress (or point) and will retain a shape after being manipulated during injection in a manner somewhat similar to fat.

The present invention may be administered anywhere in the body of animals where a bulking agent is needed (e.g., intradermally, subcutaneously, intramuscularly and submucosally) in a therapeutic amount to provide the desired cosmetic or prosthetic effect. These microdispersions may be used in humans and a variety of animals including domestic animals such as dogs, cats, cattle, sheep, horses and primates.

Many nontoxic bioabsorbable copolymers and terpolymers, that are fluids at body temperature, may be used as the fluid carrier for the injectable microdispersion. These polymers are characteristically noncrystalline polymers with glass transition temperatures of 10° C. or less. In particular, there are many polymers composed of in the range of from about 65 mole percent to about 35 mole percent of ε-caprolactone, trimethylene carbonate, ether lactone (which for the purpose of this invention is defined to be 1,4-dioxepan-2-one and 1,5-dioxepan-2-one) repeating units or combinations thereof with the remainder of the polymer being second lactone repeating units produced by a monomer selected from the group consisting of glycolide, lactide (which for the purpose of this invention also includes D-lactide, L-lactide and D,L-lactide), p-dioxanone and combinations thereof, that are liquids at body temperature. Additionally, ε-caprolactone, trimethylene carbonate, or an ether lactone may be copolymerized to provide a noncrystalline liquid copolymer. Preferred are liquid copolymers composed of in the range of from about 65 mole percent to about 35 mole percent ε-caprolactone or an ether lactone repeating units with the remainder of the copolymer being trimethylene carbonate repeating units. The liquid polymers may be linear, branched, or star branched; statistically random copolymers, terpolymers, or the like; amorphous block copolymers, terpolymers, or the like. Examples of suitable terpolymers are terpolymers selected from the group consisting of poly (glycolide-co-ε-caprolactone-co-p-dioxanone) and poly(lactide-co-ε-caprolactone-co-p-dioxanone) wherein the mole percent of ε-caprolactone repeating units is from about 35 to about 65 mole percent. Preferred are terpolymers having in the range of from 40 to 60 mole percent of ε-caprolactone repeating units. These polymers will also be purified to substantially remove unreacted monomers which may cause an inflammatory reaction in tissue.

Most preferred are liquid polymer carriers selected from the group consisting of poly(ε-caprolactone-co-trimethylene carbonate), poly(lactide-co-trimethylene carbonate), poly(e-caprolactone-co-p-dioxanone), poly(trimethylene carbonate-co-p-dioxanone), poly(ε-caprolactone-co-lactide), poly (lactide-co-1,5-dioxepan-2-one), and poly(1, 5-dioxepan-2-one-co-p-dioxanone), poly(lactide-co-1,4-dioxepan-2-one), and poly(1,4-dioxepan-2-one-co-p-dioxanone). The mole percent of ε-caprolactone, trimethylene carbonate or ether lactone repeating units in these polymers should be in the range of from about 35 to about 65 mole percent and preferably in the range of from 40 to 60 mole percent. Most preferably these liquid polymers will be statistically random copolymers.

The liquid copolymer carriers of this invention are characterized by being liquids at room temperature (25° C.) in the absence of solvents or the like. These liquid copolymers should have an inherent viscosity as determined in a 0.10 g/dL solution of hexafluoroisopropanol (HFIP) at 25° C. ranging from about 0.05 dL/g to about 0.5 dL/g, preferably from about 0.05 dL/g to about 0.3 dL/g, and most preferably from 0.1 dL/g to 0.2 dL/g. A liquid copolymer with an inherent viscosity below 0.05 dL/g may be soluble in body fluids, and a liquid copolymer with an inherent viscosity above 0.5 dL/g may be too viscous to be easily injected.

Many nontoxic bioabsorbable polymers that are solids at room temperature, may be used as the particulate material in the injectable microdispersions. The particulate materials of this invention are generally characterized as being solids at room temperature (25° C.) and preferably for some applications will be solids at body temperature (37° C.). Suitable bioabsorbable polymers include solid homopolymers poly (ε-caprolactone), poly(p-dioxanone), or poly(trimethylene carbonate) and copolymers of ε-caprolactone and trimethylene carbonate. Copolymers of ε-caprolactone should be composed of from about 100 mole percent to about 70 mole percent and preferably from 95 mole percent to 85 mole percent of ε-caprolactone repeating units with the remainder of the polymer being a plurality of second lactone repeating units. The second lactone repeating units will be selected from the group consisting of glycolide repeating units, lactide repeating units, 1,4-dioxanone repeating units, 1,4-dioxepan-2-one repeating units, 1,5-dioxepan-2-one repeating units, trimethylene carbonate repeating units, and combinations thereof. Preferred are copolymers of ε-caprolactone that are semicrystalline solids at body temperature. The solid polymers of trimethylene carbonate should be composed of from in the range of from about 1 to about 20 mole percent or from about 100 to about 80 mole percent of trimethylene carbonate with the remainder of the copolymer being composed of a plurality of lactone repeating units selected from the group consisting of glycolide repeating units, lactide repeating units, p-dioxanone repeating units, ε-caprolactone repeating units, and combinations thereof. It is preferred for the trimethylene carbonate copolymers to have crystalline regions formed by the second lactone repeating units wherein the crystalline regions provide at least 5 percent crystallinity to the final copolymer. The solid polymers may be linear, branched, or star branched; block copolymers or terpolymers; segmented block copolymers or terpolymers. These polymers will also be purified to substantially remove unreacted monomers which may cause an inflammatory reaction in tissue.

The most preferred polymers for use as the particulate material are semicrystalline polymers selected from the group consisting of poly(ε-caprolactone), poly(ε-caprolactone-co-trimethylene carbonate), poly(ε-caprolactone-co-lactide), and poly(ε-caprolactone-co-p-dioxanone). The mole percent of ε-caprolactone repeating units in these polymers should be in the range of from 100 to about 80 mole percent and preferably in the range of from 95 to 85 mole percent. Most preferably these polymers will be statistically random copolymers.

The polymers used as the particulate material should have an inherent viscosity as determined in a 0.1 g/dL solution of HFIP at 25° C. ranging from about 0.1 dL/g to about 0.8 dL/g, preferably from about 0.1 dL/g to about 0.5 dL/g, and most preferably from 0.15 dL/g to 0.3 dL/g. A polymer with an inherent viscosity below 0.1 dL/g may fail to crystallize at room temperature, and a polymer with an inherent viscosity above 0.8 dL/g may make the microdispersion too viscous to be easily administered.

These polymers may be formed in a ring opening polymerization reaction. Currently, it is preferred to initiate the ring opening polymerization with high boiling alcohols (such as 1-dodecanol), diols and triols (such as 1,2-propanediol, 1,3-propanediol, diethylene glycol, or glycerol) or polyols (such as polyethyleneglycols, polypropyleneglycols and polyethylenepropyleneglycols). Additionally, some of the monomers described above may be replaced by an equivalent amount of the corresponding acid (such as the substitution of two equivalents of glycolic acid for glycolide or two equivalents of L-lactic acid for L-lactide).

The microdispersions may contain varying amounts of the liquid carrier and the particulate material depending on the specific properties that the microdispersion is desired to have. Generally, the weight percent of fluid carrier in the microdispersion should be in the range of from about 20 to about 99 weight percent with the remainder being the particulate material. Preferably, the weight percent of fluid carrier in the microdispersion should be in the range of from about 30 to about 90 weight percent with the remainder being the particulate material. Most preferably the weight percent of fluid carrier in the microdispersion should be in the range of from about 50 to about 80 percent with the remainder being particulate material.

The viscosity of the microdispersion may also vary depending on the relative amounts of the fluid carrier and the particulate material in the microdispersion as well as on the composition of the polymers used as the liquid carrier and the particulate material. Generally, the shear viscosity of the microdispersion will be less than 10,000 poise and preferably will be in the range of from about 20 poise to about 2,000 poise as determined by capillary rheometry.

The microdispersions can be formed by physically blending the fluid carrier with the finely ground powder of the particulate material or by grinding a suspension of large pieces of the particulate material using the fluid carrier as a lubricant until the desired particle size distribution is obtained. Generally, the particulate material will have an average particle diameter of less than about 500 microns and preferably less than 50 microns. However, it is currently preferred to mix the particulate material and the liquid carrier and raise the temperature of the blend to a temperature sufficient to melt the particulate material (melt blending). Melt blending is preferred because it simplifies the mixing operation involved in producing the microdispersion. However, it is desirable to avoid excessive heating during melt blending to avoid transesterification of the polymers.

The injectable microdispersions can be used for a variety of soft tissue repair and augmentation procedures. For example, the microdispersions can be used in facial tissue repair or augmentation including but not limited to camouflaging scars, filling depressions, smoothing out irregularity, correcting asymmetry in facial hemiatrophy, second branchial arch syndrome, facial lipodystrophy and camouflaging age-related wrinkles as well as augmenting facial eminences (lips, brow, etc.). Additionally, these injectable microdispersions can be used to restore or improve sphincter function such as for treating stress urinary incontinence. Other uses of these injectable microdispersions may also include the treatment of vesicoureteral reflux (incomplete function of the inlet of the ureter in children) by subureteric injection and the application of these microdispersions as general purpose fillers in the human body.

Surgical applications for an injectable, biodegradable microdispersion include, but are not limited to: facial contouring (frown or glabellar line, acne scars, cheek depressions, vertical or perioral lip lines, marionette lines or oral commissures, worry or forehead lines, crow's feet or periorbital lines, deep smile lines or nasolabial folds, smile lines, facial scars, lips and the like); periurethral injection including injection into the submucosa of the urethra along the urethra, at or around the urethral-bladder junction to the external sphincter; ureteral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue which can be augmented for cosmetic or therapeutic effect. Surgical specialists which would use such a product include, but are not limited to, plastic and reconstructive surgeons; dermatologists; facial plastic surgeons, cosmetic surgeons, otolaryngologists; urologists; gynecologists; gastroenterologists; ophthalmologists; and any other physician qualified to utilize such a product.

Additionally, to facilitate the administration and treatment of patients with the inventive microdispersion pharmaceutically active compounds or adjuvants can be administered therewith. Pharmaceutically active agents that may be coadministered with the inventive microdispersion include but are not limited to anesthetics (such as lidocaine) and antiinflammatories (such as cortisone).

The microdispersion can be administered with a syringe and needle or a variety of devices. Several delivery devices have been developed and described in the art to administer viscous liquids such as the carpule devices described by Dr. Orentriech in U.S. Pat. Nos. 4,664,655 and 4,758,234 which are hereby incorporated by reference. Additionally, to make delivery of the microdispersion as easy as possible for the doctors, a leveraged injection rachet mechanism or powered deliver mechanism may be used. It is currently preferred for the microdispersion to be preloaded in a cylindrical container or cartridge having two ends. The first end would be adapted to receive a plunger and would have a movable seal placed therein. The second end or outlet would be covered by a removable seal and be adapted to fit into a needle housing to allow the microdispersion in the container to exit the outlet and enter a needle or other hollow tubular member of the administration device. It is also envisioned that the microdispersion could be sold in the form of a kit comprising a device containing the microdispersion. The device having an outlet for said microdispersion, an ejector for expelling the microdispersion and a hollow tubular member fitted to the outlet for administering the microdispersion into an animal.

In another embodiment of the present invention, the microdispersion may be used to coat a surface of a surgical article to enhance the lubricity of the coated surface. The polymer may be applied as a coating using conventional techniques. For example, the microdisperion may be applied by brushing or spraying the microdispersion on the device or the microdispersion may be solubilized in a dilute solution of a volatile organic solvent, e.g. acetone, methanol, ethyl acetate or toluene, and then the article can be immersed in the solution to coat its surface. Once the surface is coated, the surgical article can be removed from the solution where it can be dried at an elevated temperature until the solvent is removed.

Although it is contemplated that numerous surgical articles (including but not limited to catheters, staples and endoscopic instruments such as trocars) can be coated with the polymer of this invention to improve the surface properties of the article, the preferred surgical articles are surgical sutures, trocars and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, $\epsilon$-caprolactone, 1,4-dioxanone, and trimethylene carbonate. The preferred suture is a braided multifilament suture composed of polyglycolide or poly(glycolide-co-lactide). It will be readily appreciated that the coating may likewise be used with good results on absorbable monofilament sutures as well as on nonabsorbable monofilament and multifilament sutures. Nonabsorbable sutures such as cotton, linen, silk, nylon, polyethylene terephthalate and polyolefins are normally coated with nonabsorbable compositions. Polyolefins are usually of monofilament construction while cotton, linens, silk and polyester are usually of braided, twisted or covered multifilament construction.

The amount of microdispersion to be applied on the surface of a braided suture can be readily determined empirically, and will depend on the particular copolymer and suture chosen. Ideally, the amount of microdispersion applied to the surface of the suture may range from about 0.5 to about 30 percent of the weight of the coated suture, more preferably from about 1.0 to about 20 weight percent, most preferably from 1 to about 5 parts by weight. If the amount of coating on the suture were greater than about 30 weight percent, then it may increase the risk that the coating may flake off when the suture is passed through tissue.

Sutures coated with the microdisperion polymers of this invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the microdisperion of this invention.

In another embodiment of the present invention when the article is a surgical needle, or trocars, the amount of coating applied to the surface of the article is an amount which creates a layer with a thickness ranging preferably between about 2 to about 20 microns on the needle, or trocars, more preferably about 4 to about 8 microns. If the amount of coating on the needle or trocars were such that the thickness of the coating layer was greater than about 20 microns, or if the thickness was less than about 2 microns, then the desired performance of the needle or trocars as it is passed through tissue may not be achieved.

The following nonlimiting examples are provided to further illustrate the practice of the present invention.

EXAMPLES

Example 1

LIQUID POLYMERS OF $\epsilon$-CAPROLACTONE/L-LACTIDE AT 50/50 INITIAL MOLE COMPOSITION A flame dried, 250 mL, round bottom single neck flask was charged with 57.1 grams (0.50 mole) of $\epsilon$-caprolactone, 72.1 grams (0.50 mole) of L-lactide, 4.00 mL (55 mmol) of distilled glycerol, and 0.10 mL (34 μmol) of a 0.33 M stannous octoate solution in toluene. The flask was fitted with a flame dried mechanical stirrer. The reactor was purged with nitrogen three times before venting with nitrogen. The reaction mixture was heated to 160° C. and maintained at this temperature for about 18–20 hours. The copolymer was dried under vacuum (0.1 mm Hg) at 110° C. for about 16 hours to remove any unreacted monomer. The copolymer had an inherent viscosity of 0.14 dL/g in hexafluoroisoproponal (HFIP) at 25° C. The copolymer was a liquid at room temperature. The molar ratio of PCL/PLA was found to be 53.7/46.3 by proton NMR.

Example 2

LIQUID POLYMERS OF $\epsilon$-CAPROLACTONE/L-LACTIDE AT 50/50 INITIAL MOLE COMPOSITION The procedure in Example 1 was substantially repeated, except that 13.6 mL of 1-dodecanol instead of 4.00 mL of glycerol and 0.12 mL (40 μmol) instead of 0.10 mL of stannous octoate solution were used. The copolymer was dried under vacuum (0.1 mm Hg) at 110° C. for about 16 hours to remove any unreacted monomer. The copolymer had an inherent viscosity of 0.15 dL/g in HFIP at 25° C. The copolymer was viscous liquid at room temperature. The molar ratio of PCL/PLA was found to be 51.5/48.5 by proton NMR.

Example 3

LIQUID POLYMERS OF $\epsilon$-CAPROLACTONE/L-LACTIDE AT 50/50 INITIAL MOLE COMPOSITION The procedure in Example 2 was substantially repeated, except that 5.6 mL of 1-dodecanol was used instead of 13.6 mL. The copolymer was dried under vacuum (0.1 mm Hg) at 110° C. for about 16 hours to remove any unreacted monomer. The copolymer had an inherent viscosity of 0.28 dL/g in HFIP at 25° C. The copolymer was very a viscous liquid at room temperature. The molar ratio of PCL/PLA was found to be 50.5/49.5 by proton NMR.

Example 4

LIQUID POLYMERS OF $\epsilon$-CAPROLACTONE/L-LACTIDE AT 50/50 INITIAL MOLE COMPOSITION The procedure in Example 3 was substantially repeated, except that 4.4 mL (60 mmol) propylene glycol (USP grade) was used instead of 5.6 mL of 1-dodecanol. The copolymer had an inherent viscosity of 0.17 dL/g in HFIP at 25° C.

Example 5A

LIQUID POLYMERS OF $\epsilon$-CAPROLACTONE/p-DIOXANONE AT 50/50 INITIAL MOLE COMPOSITION A flame dried, 250 mL, round bottom single neck flask was charged with 57.1 grams (0.50 mole) of $\epsilon$-caprolactone, 51.0 grams (0.50 mole) of p-dioxanone, 4.00 mL (55 mmol) of distilled glycerol, and 0.12 mL (40 μmol) of a 0.33 M stannous octoate solution in toluene. The flask was fitted with a flame dried mechanical stirrer. The flask was purged with nitrogen three times before venting with nitrogen. The reaction mixture was heated to 140° C. and maintained at this temperature for about 24 hours. The reaction mixture was then cooled to 110° C. and maintained at this temperature for 24 hours. The copolymer was dried under vacuum (0.1 mm Hg) at 80° C. for about 32 hours to remove any unreacted monomer. The copolymer had an inherent viscosity of 0.14 dL/g in HFIP at 25° C. The copolymer was a liquid at room temperature. The molar ratio of PCL/PDS was found to be 53.2/46.8 by proton NMR.

Example 5B

LIQUID POLYMERS OF $\epsilon$-CAPROLACTONE/p-DIOXANONE AT 50/50 INITIAL MOLE COMPOSITION A flame dried, 250 mL, round bottom single neck flask was charged with 57.1 g (0.50 mole) of $\epsilon$-caprolactone, 51.0 grams (0.50 mole) of p-dioxanone, 3.7 mL (50 mmol) of propylene glycol (USP), and 0.12 mL (34 μmol) of a 0.33 M stannous octoate solution in toluene. The flask was fitted with a flame dried mechanical stirrer. The flask was purged with nitrogen three times before venting with nitrogen. The reaction mixture was heated to 140° C. and maintained at this temperature for about 24 hours and then bath temperature was lowered to 110° C. and maintained at this temperature for 24 hours. The copolymer was dried under vacuum (0.1 mm Hg) at 80° C. for about 32 hours to remove any unreacted monomer. The copolymer had an inherent viscosity of 0.22 dL/g in HFIP at 25° C. The copolymer was a liquid at room temperature. The molar ratio of PCL/PDS was found to be 52.4/47.6 by proton NMR.

Example 5C

LIQUID POLYMERS OF $\epsilon$-CAPROLACTONE/p-DIOXANONE AT 60/40 INITIAL MOLE COMPOSITION The procedure in Example 5A was substantially repeated, except that 68.48 grams (0.60 mole) of $\epsilon$-caprolactone and 40.83 grams (0.40 mole) of p-dioxanone were used. The copolymer was dried under vacuum (0.1 mm Hg) at 80° C. for about 80 hours to remove any unreacted monomer. The copolymer had an inherent viscosity of 0.19 dL/g in HFIP at 25° C. The copolymer was a liquid at room temperature. The molar ratio of PCL/PDS was found to be 57.2/42.8 by proton NMR.

Example 5D

LIQUID POLYMERS OF $\epsilon$-CAPROLACTONE/p-DIOXANONE AT 40/60 INITIAL MOLE COMPOSITION The procedure in Example 5A is substantially repeated except that 45.7 grams (0.40 mole) of $\epsilon$-caprolactone and 61.3 grams (0.60 mole) of p-dioxanone were used. The copolymer was dried under vacuum (0.1 mm Hg) at 80° C. for about 80 hours to remove any unreacted monomer. The copolymer had an inherent viscosity of 0.18 dL/g in HFIP at 25° C. The copolymer was a liquid at room temperature. The molar ratio of PCL/PDS was found to be 46.7/53.3 by proton NMR.

Example 6

LIQUID POLYMERS OF $\epsilon$-CAPROLACTONE/p-DIOXANONE AT 50/50 INITIAL MOLE COMPOSITION The procedure in Example 5A was substantially repeated except that 13.6 mL 1-dodecanol was used instead of 4.00 mL of glycerol. The copolymer was dried under vacuum (0.1 mm Hg) at 80° C. for about 32 hours to remove any unreacted monomer. The copolymer had an inherent viscosity of 0.16 dL/g in HFIP at 25° C. The copolymer was a liquid at room temperature.

Example 7

LIQUID POLYMERS OF $\epsilon$-CAPROLACTONE/p-DIOXANONE AT 50/50 INITIAL MOLE COMPOSITION The procedure in Example 5A was substantially repeated except that 6.8 mL instead of 13.6 mL 1-dodecanol was used. The copolymer was dried under vacuum (0.1 mm Hg) at 80° C. for about 16 hours to remove any unreacted monomer. The copolymer had an inherent viscosity of 0.24 dL/g in HFIP at 25° C. The copolymer was a viscous liquid at room temperature. The molar ratio of PCL/PDS was found to be 53.6/46.4 by proton NMR.

Example 8

LIQUID POLYMERS OF $\epsilon$-CAPROLACTONE/p-DIOXANONE AT 50/50 INITIAL MOLE COMPOSITION The procedure in Example 7 was substantially repeated except that 4.4 mL (60 mmol) of propylene glycol (USP) was used instead of 6.8 mL of 1-dodecanol. The copolymer was dried under vacuum (0.1 mm Hg) at 80° C. for about 16 hours to remove any unreacted monomer. The copolymer had an inherent viscosity of 0.17 dL/g in HFIP at 25° C. The copolymer was a viscous liquid at room temperature.

Example 9

LIQUID POLYMERS OF $\epsilon$-CAPROLACTONE/ TRIMETHYLENE CARBONATE AT 50/50 INITIAL MOLE COMPOSITION A flame dried, 250 mL, round bottom single neck flask was charged with 57.1 grams (0.50 mole) of $\epsilon$-caprolactone, 51.0 grams (0.50 mole) of trimethylene carbonate, 4.4 mL (60 mmol) of propylene glycol (USP), and 0.10 mL (34 $\mu$mol) of a 0.33 M solution of stannous octoate in toluene. The flask was fitted with a flame dried mechanical stirrer. The flask was purged with nitrogen three times before venting with nitrogen. The reaction mixture was heated to 160° C. and maintained at this temperature for about 18–20 hours. The copolymer was dried under vacuum (0.1 mm Hg) at 80° C. for about 16 hours to remove any unreacted monomer. The copolymer had an inherent viscosity of 0.20 dL/g in HFIP at 25° C. The copolymer was a viscous liquid at room temperature.

Example 10

HOMOPOLYMER OF $\epsilon$-CAPROLACTONE WITH 1-DODECANOL AS THE INITIATOR

A flame dried, 250 mL, round bottom single neck flask was charged with 114.1 grams (1.0 mole) of $\epsilon$-caprolactone, 9.1 mL of 1-dodecanol, and 0.10 mL (34 $\mu$mol) of a 0.33 M stannous octoate solution in toluene. The flask was fitted with a flame dried mechanical stirrer. The flask was purged with nitrogen three times before, venting with nitrogen. The reaction mixture was heated to 190° C. and maintained at this temperature for about 18–20 hours. The copolymer had an inherent viscosity of 0.24 dL/g in HFIP at 25° C. The copolymer was a low melting solid (53–56° C. by Fisher Johns). The molar ratio of PCL/E-caprolactone was found to be 98.2/1.8 by proton NMR.

Example 11

HOMOPOLYMER OF $\epsilon$-CAPROLACTONE WITH PROPYLENE GLYCOL AS THE INITIATOR

The procedure in Example 9 was substantially repeated except that 2.9 mL (40 mmol) of propylene glycol was used instead of 9.1 mL of 1-dodecanol. The copolymer had an inherent viscosity of 0.25 dL/g in HFIP at 25° C. The copolymer was a low melting solid (55–58° C. by Fisher Johns). The molar ratio of PCL/E-caprolactone was found to be 98.2/1.8 by proton NMR.

Example 12

COPOLYMER OF $\epsilon$-CAPROLACTONE/p-DIOXANONE AT 99/5 INITIAL MOLE COMPOSITION WITH PROPYLENE GLYCOL AS THE INITIATOR A flame dried, 250 mL, round bottom single neck flask was charged with 108.4 grams (0.99 mole) of ε-caprolactone, 5.10 grams (0.05 mole) p-dioxanone, 2.9 mL (40 mmol) propylene glycol (USP), and 0.10 mL (34 μmol) of a 0.33 M stannous octoate solution in toluene. The flask was fitted with a flame dried mechanical stirrer. The flask was purged with nitrogen three times before venting with nitrogen. The reaction mixture was heated to 160° C. and maintained at this temperature for about 24 hours, and then the bath temperature was dropped to 100° C. and maintained there for 24 hours. The copolymer has an inherent viscosity of 0.29 dL/g in HFIP at 25° C. The copolymer was a low melting solid (43–47° C. by Fisher Johns). The molar ratio of PCL/PDS was found to be 99.1/4.9 by proton NMR.

Example 13

COPOLYMER OF ε-CAPROLACTONE/p-DIOXANONE AT 90/10 INITIAL MOLE COMPOSITION WITH PROPYLENE GLYCOL AS THE INITIATOR

A flame dried, 250 mL, round bottom single neck flask was charged with 102.7 grams (0.90 mole) of ε-caprolactone, 10.2 grams (0.10 mole) p-dioxanone, 2.9 mL (40 mmol) of propylene glycol (USP), and 0.10 mL (34 μmol) of a 0.33 M stannous octoate solution in toluene. The flask was fitted with a flame dried mechanical stirrer. The flask was purged with nitrogen three times before venting with nitrogen. The reaction mixture was heated to 160° C. and maintained at this temperature for about 24 hours, and then the bath temperature was dropped to 100° C. and maintained there for 24 hours. The copolymer had an inherent viscosity of 0.23 dL/g in HFIP at 25° C. The copolymer was a low melting solid (38–41° C. by Fisher Johns). The molar ratio of PCL/PDS was found to be 90.0/10.0 by proton NMR.

Example 14

COPOLYMER OF ε-CAPROLACTONE/p-DIOXANONE AT 80/20 INITIAL MOLE COMPOSITION WITH PROPYLENE GLYCOL AS THE INITIATOR

A flame dried, 250 mL, round bottom single neck flask was charged with 91.3 grams (0.80 mole) of ε-caprolactone, 20.4 grams (0.20 mole) p-dioxanone, 2.9 mL (40 mmol) of propylene glycol (USP), and 0.10 mL (34 μmol) of a 0.33 M stannous octoate solution in toluene. The flask was fitted with a flame dried mechanical stirrer. The flask was purged with nitrogen three times before venting with nitrogen. The reaction mixture was heated to 160° C. and maintained at this temperature for about 24 hours, and then the bath temperature was dropped to 100° C. and maintained there for 24 hours. The copolymer has an inherent viscosity of 0.25 dL/g in HFIP at 25° C. The copolymer was a low melting solid (28–30° C. by Fisher Johns). The molar ratio of PCL/PDS was found to be 81.9/18.1 by proton NMR.

Example 15

COPOLYMER OF ε-CAPROLACTONE/L-LACTIDE AT 99/5 INITIAL MOLE COMPOSITION WITH PROPYLENE GLYCOL AS THE INITIATOR

A flame dried, 250 mL, round bottom single neck flask was charged with 108.4 grams (0.99 mole) of ε-caprolactone, 7.20 g (0.05 mole) L-lactide, 2.6 mL (35 mmol) of propylene glycol (USP), and 0.10 mL (34 μmol) of a 0.33 M stannous octoate solution in toluene. The flask was fitted with a flame dried mechanical stirrer. The flask was purged with nitrogen three times before venting with nitrogen. The reaction mixture was heated to 160° C. and maintained at this temperature for about 18 hours. The copolymer had an inherent viscosity of 0.24 dL/g in HFIP at 25° C. The copolymer was a low melting solid (45–47° C. by Fisher Johns). The molar ratio of PCL/PLA was found to be 98.8/1.2 by proton NMR.

Example 16

COPOLYMER OF ε-CAPROLACTONE/L-LACTIDE AT 90/10 INITIAL MOLE COMPOSITION WITH GLYCEROL AS THE INITIATOR

A flame dried, 250 mL, round bottom single neck flask was charged with 102.7 grams (0.90 mole) of ε-caprolactone, 14.4 grams (50 mmol) L-lactide, 1.8 mL (25 mmol) of glycerol (USP), and 0.10 mL (34 μmol) of a 0.33 M stannous octoate solution in toluene. The flask was fitted with a flame dried mechanical stirrer. The flask was purged with nitrogen three times before venting with nitrogen. The reaction mixture was heated to 160° C. and maintained at this temperature for about 18 hours. The copolymer was dried under vacuum (0.1 mm Hg) at 80° C. for about 28 hours to remove any unreacted monomer. The copolymer has an inherent viscosity of 0.30 dL/g in HFIP at 25° C. The copolymer was a low melting solid (32–36° C. by Fisher Johns). The molar ratio of PCL/PLA was found to be 93.0/7.0 by proton NMR.

Example 17

COPOLYMER OF ε-CAPROLACTONE/L-LACTIDE AT 90/10 INITIAL MOLE COMPOSITION WITH PROPYLENE GLYCOL AS THE INITIATOR

The procedure in Example 15 was substantially repeated, except that 2.6 mL (35 mmol) of propylene glycol was used instead of 1.8 mL of glycerol. The copolymer was isolated and characterized. The copolymer has an inherent viscosity of 0.28 dL/g in HFIP at 25° C. The copolymer was a low melting solid (36–41° C. by Fisher Johns). The molar ratio of PCL/PLA was found to be 90.9/9.1 by proton NMR.

Example 18

COPOLYMER OF ε-CAPROLACTONE/L-LACTIDE AT 90/10 INITIAL MOLE COMPOSITION WITH PENTAERYTHRITOL AS THE INITIATOR

The procedure in Example 15 was substantially repeated except that 3.40 grams (25 mmol) of pentaerythritol was used instead of 1.8 mL of glycerol. The copolymer was isolated and characterized. The copolymer had an inherent viscosity of 0.26 dL/g in HFIP at 25° C. The copolymer was a low melting solid (32–35° C. by Fisher Johns). The molar ratio of PCL/PLA was found to be 93.4/6.6 by proton NMR.

Example 19

COPOLYMERS OF ε-CAPROLACTONE/TRIMETHYLENE CARBONATE AT 90/10 INITIAL MOLE COMPOSITION

A flame dried, 250 mL, round bottom single neck flask was charged with 102.7 grams (0.90 mole) of ε-caprolactone, 10.2 grams (0.10 mole) of trimethylene carbonate, 2.9 mL (40 mmol) of propylene glycol (USP), and 0.10 mL (34 μmol) of a 0.33 M stannous octoate solution in toluene. The flask was fitted with a flame dried mechanical stirrer. The flask was purged with nitrogen three times before venting with nitrogen. The reaction mixture was heated to 160° C. and maintained at this temperature for about 18–20 hours. The copolymer was dried under vacuum (0.1 mm Hg) at 80° C. for about 16 hours to remove any unreacted monomer. The copolymer had an inherent viscosity of 0.25 dL/g in HFIP at 25° C. The copolymer was a viscous liquid at room temperature.

Example 20

VISCOSITY OF LIQUID ABSORBABLE COPOLYMERS

This example presents viscosity data on liquid absorbable polymers which were prepared in a manner similar to that described in Examples 1–9.

The viscosity of the polymers were determined by capillary rheometry. The viscosity data for the liquid absorbable polymers are presented in Tables 1, 2, and 3.

TABLE 1

Viscosity Data on Liquid Absorbable Copolymer of ε-Caprolactone and p-Dioxanone

| Sample No. | Copolymer Composition in Mole Percents[1] | | Inherent Viscosity[2] (dL/g) | Viscosity in Poise | |
|---|---|---|---|---|---|
| | ε-Caprolactone | p-Dioxanone | | @37° C. | @23° C. |
| 1 | 50 | 50 | 0.08 | 16 | 43 |
| 2 | 50 | 50 | 0.09 | 12 | 34 |
| 3 | 50 | 50 | 0.14 | 32 | 86 |
| 4 | 50 | 50 | 0.14 | 16 | 37 |
| 5 | 50 | 50 | 0.16 | 22 | 49 |
| 6 | 50 | 50 | 0.17 | 31 | 78 |
| 7 | 50 | 50 | 0.22 | 92 | 255 |
| 8 | 50 | 50 | 0.24 | 106 | 279 |
| 9 | 60 | 40 | 0.14 | 20 | 51 |
| 10 | 60 | 40 | 0.14 | 19 | 45 |
| 11 | 60 | 40 | 0.15 | 20 | 47 |
| 12 | 70 | 30 | 0.16 | 18 | 42 |
| 13 | 70 | 30 | 0.16 | 15 | 32 |
| 14 | 70 | 30 | 0.16 | 15 | 35 |

[1]Based on the initial composition in the polymerization reaction.
[2]The inherent viscosity was determined in a 0.1 dL/g solution of HFIP at 25° C.

TABLE 2

Viscosity Data on Liquid Absorbable Copolymers 50:50 (mol/mol)Poly[ε-Caprolactone-co-L-Lactide][1]

| Sample No. | Inherent Viscosity[2] (dL/g) | Viscosity in Poise | |
|---|---|---|---|
| | | @37° C. | @23° C. |
| 1 | 0.06 | 49 | 216 |
| 2 | 0.08 | 98 | 461 |
| 3 | 0.09 | 102 | 442 |
| 4 | 0.09 | 93 | 396 |
| 5 | 0.12 | 179 | 919 |
| 6 | 0.14 | 370 | 1,985 |
| 7 | 0.15 | 377 | 1,786 |
| 8 | 0.13 | 193 | 901 |
| 9 | 0.14 | 198 | 945 |
| 10 | 0.17 | 317 | 1,286 |
| 11 | 0.16 | 448 | 2,344 |
| 12 | 0.17 | 892 | 5,407 |
| 13 | 0.28 | 4,903 | 23,004 |

[1]Based on the initial composition in the polymerization reaction.
[2]The inherent viscosity was determined in a 0.1 dL/g solution of HFIP at 25° C.

TABLE 3

Viscosity Data on Liquid Absorbable Polymers 50:50 (mol/mol)Poly[ε-caprolactone-co-trimethylene carbonate][1]

| Sample No. | Inherent Viscosity[2] (dL/g) | Viscosity in Poise | |
|---|---|---|---|
| | | @37° C. | @23° C. |
| 1 | 0.2 | 87 | 216 |
| 2 | 0.18 | 69 | 178 |
| 3 | 0.13 | 42 | 106 |
| 4 | 0.16 | 37.6 | 102.4 |
| 5 | 0.16 | 41.1 | 105.0 |
| 6 | 0.14 | 32.5 | 86.6 |
| 7 | 0.14 | 34.0 | 90.1 |
| 8 | 0.13 | 23.7 | 60.6 |
| 9 | 0.13 | 20.2 | 51.5 |
| 10 | 0.13 | 21.1 | 54.9 |
| 11 | 0.13 | 27.2 | 69.4 |
| 12 | 0.14 | 47.7 | 120.4 |
| 13 | 0.15 | 43.8 | 110.4 |
| 14 | 0.13 | 29.3 | 72.9 |
| 15 | 0.13 | 27.5 | 69.1 |
| 16 | 0.15 | 49.9 | 127.5 |
| 17 | 0.14 | 33.8 | 84.3 |
| 18 | 0.14 | 35.1 | 87.4 |
| 19 | 0.14 | 34.8 | 85.8 |
| 20 | 0.13 | 35.8 | 89.0 |
| 21 | 0.1 | 17.3 | 41.6 |
| 22 | 0.09 | 8.0 | 17.8 |
| 23 | 0.15 | 44.6 | 114.0 |

[1]Based on the initial composition in the polymerization reaction.
[2]The inherent viscosity was determined in a 0.1 dL/g solution of HFIP at 25° C.

Example 21

This example presents data on low melt polymers which were prepared in a manner similar to that described in Examples 10–19.

The melting points of these polymers were determined by using a Fisher-Johns melting point apparatus and are listed in Tables 4 and 5.

TABLE 4

Low Melting Polymers of
ε-Caprolactone and Trimethylene Carbonate

| Sample No. | Copolymer Composition in Mole Percents[1] | | Inherent Viscosity[2] (dL/g) | Melting Point (° C.) |
|---|---|---|---|---|
| | ε-Caprolactone | Trimethylene Carbonate | | |
| 1 | 95 | 5 | 0.22 | 45–48 |
| 2 | 90 | 10 | 0.25 | 39–41 |
| 3 | 90 | 10 | 0.27 | 39 |
| 4 | 90 | 10 | 0.28 | 40 |
| 5 | 90 | 10 | 0.32 | 39 |
| 6 | 90 | 10 | 0.2 | 43–45 |
| 7 | 90 | 10 | 0.24 | 44–48 |

[1]Based on the initial composition in the polymerization reaction.
[2]The inherent viscosity was determined in a 0.1 dL/g solution of HFIP at 25° C.

TABLE 5

Low Melting Polymers of
ε-Caprolactone and L-Lactide

| Sample No. | Copolymer Composition in Mole Percents[1] | | Inherent Viscosity[2] (dL/g) | Melting Point (° C.) |
|---|---|---|---|---|
| | ε-Caprolactone | L-Lactide | | |
| 1 | 95 | 5 | 0.24 | 45–47 |
| 2 | 90 | 10 | 0.3 | 32–36 |
| 3 | 90 | 10 | 0.28 | 36–41 |
| 4 | 90 | 10 | 0.26 | 32–35 |
| 5 | 90 | 10 | 0.23 | 36–39 |
| 6 | 90 | 10 | 0.22 | 36–38 |

[1]Based on the initial composition in the polymerization reaction.
[2]The inherent viscosity was determined in a 0.1 dL/g solution of HFIP at 25° C.

Example 22

PREPARATION OF A MICRODISPERSION

This example illustrates the preparation of microdispersions by melt blending that are suitable for use as injectable microdispersions for soft tissue repair and augmentation: 6.0 grams of a 50:50 (mol/mol) poly(ε-caprolactone-co-trimethylene carbonate) similar to the copolymer described in Example 9 and 4.0 grams of a 90:10 (mol/mol) poly(ε-caprolactone-co-trimethylene carbonate) similar to the copolymer described in Example 19 were transferred into a clean, flame dried 25 mL round bottom flask and stirred magnetically at 75° C. to 80° C. for one hour under an inert atmosphere of dry nitrogen gas. The resulting microdispersion had an inherent viscosity of 0.21 dL/g in HFIP at 25° C.

Example 23

RHEOLOGY OF A MICRODISPERSION

This example demonstrates the shear thinning nature of injectable microdispersion for soft tissue augmentation.

The microdispersion described as the blend in Example 22 was placed between 40 mm diameter parallel plates in a Rheometries RDA II dynamic mechanical analyzer. The dynamic viscosity was measured at 26.5, 38, 48.3 and 60° C. from 0.1 to 100 sec$^{-1}$. The sample gap was 1.0 mm and the strain was varied from 5 to 25% so that the 2000 g-cm torque rebalance transducer had sufficient signal to be within specification. The data from this experiment are presented in FIG. 1.

The results of this experiment show the shear thinning nature of the dispersion below the melting point of the particulate material. At 26.5° C. the viscosity drops from 2,360,000 poise at 0.1 sec$^{-1}$ to 11,270 poise at 100 sec$^{-1}$. At 38° C. the viscosity drops from 130,000 poise at 0.1 sec$^-$. to 1000 poise at 100 sec$^{-1}$. Between 38° C. and 48.3° C., the particulate material of the dispersion melted, and at 48.3° C., the viscosity was Newtonian (shear rate independent) at 22 poise and at 60° C. the viscosity was Newtonian at 12 poise. The shear thinning behavior of the microdispersions is imperative for facile delivery through a fine syringe needle. The effect of temperature, to reduce viscosity, below the melting temperature of the particulate material can be used to reduce the effort necessary to deliver the microdispersion through the needle. The retention of dispersion-like properties at and below body temperature is desirable in order to maintain the yield stress (or point) that will retain a shape after being manipulated during injection in a manner somewhat similar to fat.

Example 24

POLY(L-LACTIC ACID) OLIGOMERS

Poly(L-lactic acid) oligomers were prepared as described in Example 1 of German Patent Application DE 4,235,312 A1. For instance, 100.0 grams (0.94 mol) of an 85 weight percent solution of L-lactic acid was transferred into a clean, three neck, 250 mL round bottom flask equipped with a mechanical stirrer, a distillation head, and a stopper. The reaction vessel was evacuated using an aspirator (ca. 25 mm Hg) and then heated with an oil bath to 150° C. for five hours. 22 mL (1.2 mol) of water were collected. The hot poly(L-lactic acid) oligomer (A) was poured into a wide mouth jar and allowed to cool down to room temperature under a nitrogen gas atmosphere. The oligomer (A) was a highly viscous liquid having an inherent viscosity of 0.06 dL/g in HFIP at 25° C. The melt viscosity of oligomer (A) was measured on a Rheometries RDA II viscometer and was found to be 18,000 poise and Newtonian in nature at 25° C.

The above procedure was repeated except that the reaction time was increased to 24 hours. 25 mL of water were collected. The resulting oligomer (B) was a crystalline solid with a melting point range between 75° C. and 83° C. as measured on a Fisher-Johns melting point apparatus. The inherent viscosity of oligomer (B) was 0.15 dL/g in HFIP at 25° C.

A 50:50 (w/w) blend of oligomer (A) and oligomer (B) was made by transferring 20.0 grams of each oligomer into a 250 mL round bottom flask equipped with a mechanical stirrer and an adaptor with a port connected to a stream of dry nitrogen gas and a Firestone valve via tygon tubing. This mixture was heated to 160° C. for thirty minutes, transferred into a wide mouth jar, and allowed to cool down to room temperature in an inert atmosphere. The blend was a transparent, stiff material having an inherent viscosity of 0.08 dL/g in HFIP at 25° C. The blend was, in fact, a very viscous fluid at room temperature as demonstrated by its slow flow through a tube overnight. After standing at room temperature for five weeks in a jar, the bulk of the blend was still transparent; only the surface layer was translucent.

We claim:

1. A suture coated with a bioabsorbable microdispersion coating composed of:

a fluid carrier that is a liquid polymer selected from the group consisting of liquid polymers of a plurality of at least two different first lactone repeating units and liquid polymers of a plurality of first lactone and second lactone repeating units; wherein the first lactone repeating units are selected from the group consisting of $\epsilon$-caprolactone repeating units, trimethylene carbonate repeating units, ether lactone repeating units and combinations thereof and the second lactone repeating units are selected from the group consisting of glycolide repeating units, lactide repeating units, p-dioxanone repeating units and combinations thereof; and a particulate material that is selected from the group consisting of solid homopolymers of poly($\epsilon$-caprolactone), solid homopolymers of poly(p-dioxanone), solid homopolymers of poly(trimethylene carbonate), solid copolymers of a plurality of $\epsilon$-caprolactone repeating units and third lactone repeating units, solid copolymers of a plurality of trimethylene carbonate repeating units and second lactone repeating units; wherein the third lactone repeating units are selected from the group consisting of glycolide repeating units, lactide repeating units, trimethylene carbonate repeating units, p-dioxanone repeating units, 1,4-dioxepan-2-one repeating units, 1-5-dioxepan-2-one repeating units and combinations thereof.

2. The coated suture of claim 1 wherein the fluid carrier is a noncrystalline liquid polymer with an inherent viscosity of from about 0.05 dL/g to about 0.5 dL/g selected from the group consisting of polymers of from about 65 mole percent to about 35 mole percent of $\epsilon$-caprolactone repeating units with the remainder being the third lactone repeating units, polymers of from about 65 to about 35 mole percent of ether lactone repeating units with the remainder being the second lactone repeating units, polymers of from about 65 to abut 35 mole percent of trimethylene carbonate repeating units with the remainder being the second lactone repeating units and polymers of from about 65 to about 35 mole percent ether lactone repeating units with the remainder being trimethylene carbonate repeating units.

3. The coated suture of claim 2 wherein the fluid carrier is a noncrystalline liquid polymer selected from the group consisting of poly($\epsilon$-caprolactone-co-trimethylene carbonate), poly (lactide-co-trimethylene carbonate), poly ($\epsilon$-caprolactone-co-p-dioxanone), poly(trimethylene carbonate-co-p-dioxanone), poly($\epsilon$-caprolactone-co-lactide), poly(lactide-co-1,4-dioxepan-2-one), poly(1,4-dioxepan-2-one-co-p-dioxanone), poly(lactide-co-1,5-dioxepan-2-one), and poly(1,5-dioxepan-2-one-co-p-dioxanone).

4. The coated suture of claim 2 wherein the particulate material is a solid polymer of $\epsilon$-caprolactone repeating units and the third lactone repeating units and contains from about 100 to about 70 mole percent $\epsilon$-caprolactone repeating units.

5. The coated suture of claim 2 wherein the particulate material is a solid polymer of trimethylene carbonate repeating units and the second lactone repeating units and contains from about 1 to 20 mole percent trimethylene carbonate repeating units.

6. The coated suture of claim 4 wherein the particulate material is a copolymer of $\epsilon$-caprolactone repeating units and the third lactone repeating units and contains from in the range of from about 95 to about 85 mole percent $\epsilon$-caprolactone repeating units.

7. The coated suture of claim 2 wherein the particulate material is a solid polymer selected from the group consisting of poly($\epsilon$-caprolactone), poly($\epsilon$-caprolactone-co-trimethylene carbonate), poly($\epsilon$-caprolactone-co-lactide), and poly($\epsilon$-caprolactone-co-p-dioxanone).

8. The coated suture of claim 2 wherein the weight percent of the fluid carrier in microdispersion is in the range of from about 20 to about 99 weight percent with the remainder being the particulate material.

9. The coated suture of claim 2 wherein additionally present is a pharmaceutically active compound.

10. An article coated with a bioabsorbable microdispersion composed of:

a fluid carrier that is a liquid polymer selected from the group consisting of liquid polymers a plurality of at least two different first lactone repeating units and liquid polymers of a plurality of first lactone and second lactone repeating units; wherein the first lactone repeating units are selected from the group consisting of e-caprolactone repeating units, trimethylene carbonate repeating units, ether lactone repeating units and combinations thereof and the second lactone repeating units are selected from the group consisting of glycolide repeating units, lactide repeating units, p-dioxanone repeating units and combinations thereof; and a particulate material that is selected from the group consisting of solid homopolymers of poly(e-caprolactone), solid homopolymers of poly(p-dioxanone), solid homopolymers of poly(trimethylene carbonate), solid copolymers of a plurality of e-caprolactone repeating units and third lactone repeating units, solid copolymers of a plurality of trimethylene carbonate repeating units and second lactone repeating units; wherein the third lactone repeating units are selected from the group consisting of glycolide repeating units, lactide repeating units, trimethylene carbonate repeating units, p-dioxanone repeating units, 1,4-dioxepan-2-one repeating units, 1-5-dioxepan-2-one repeating units and combinations thereof.

11. The coated surgical article of claim 10 wherein the fluid carrier component of the microdispersion is a noncrystalline liquid polymer with an inherent viscosity of from about 0.05 dL/g to about 0.5 dL/g selected from the group consisting of polymers of from about 65 mole percent to about 35 mole percent of $\epsilon$-caprolactone repeating units with the remainder being the third lactone repeating units, polymers of from about 65 to about 35 mole percent of ether lactone repeating units with the remainder being the second lactone repeating units, polymers of from about 65 to about 35 mole percent of trimethylene carbonate repeating units with the remainder being the second lactone repeating units, and polymers of from about 65 to about 35 mole percent of ether lactone repeating units with the remainder being trimethylene carbonate repeating units.

12. The coated surgical article of claim 11 wherein the particulate material component of the microdispersion is a solid polymer of $\epsilon$-caprolactone repeating units and the third lactone repeating units and contains from about 100 to about 70 mole percent $\epsilon$-caprolactone repeating units.

13. The coated surgical article of claim 11 wherein the particulate material component of the microdispersion is a solid polymer trimethylene carbonate repeating unit and second lactone repeating units and contains from about 1 to about 20 mole percent trimethylene carbonate repeating units.

14. The coated surgical article of claim 11 wherein the fluid carrier component of the microdispersions is a liquid polymer selected from the group consisting of poly($\epsilon$- caprolactone-co-trimethylene carbonate), poly(lactide-co-trimethylene carbonate) poly(ε-caprolactone-co-p-dioxanone), poly(trimethylene carbonate-co-p-dioxanone), poly(ε-caprolactone-colactide), poly(lactide-co-1,4-dioxepan-2-one), poly(1,4-dioxepan-2-one-co-p-dioxanone), poly(lactide-co-1,5-dioxepan-2-one), and poly(1,5-dioxepan-2-one-co-p-dioxanone).

15. The coated surgical article of claim 11 wherein the particulate material component of the microdispersions is a copolymer of ε-caprolactone repeating units and the third lactone repeating units and contains in the range of from about 95 to about 85 mole percent of ε-caprolactone repeating units.

16. The coated surgical article of claim 11 wherein the weight percent of the fluid carrier in the microdispersion is in the range of from about 20 to about 99 weight percent with the remainder being the particulate material.

17. The coated suture of claim 1 wherein the amount of the polymer coated on the outer surface of the suture is between about 0.5 to about 30 weight percent.

18. The coated suture of claim 1 wherein the amount of the polymer coated on the outer surface of the suture is between about 1.0 to about 20 weight percent.

19. The coated suture of claim 1 wherein the suture is a synthetic absorbable suture composed of homopolymer or copolymers of lactone monomers selected from the group consisting of glycolide, lactide, ε-caprolactone, 1,4-dioxanone and trimethylene carbonate.

20. The coated suture of claim 1 wherein the suture is a synthetic absorbable, braided multifilament suture.

21. The coated suture of claim 1 wherein the suture is composed of polyglycolide or poly(glycolide-co-lactide).

22. The coated surgical article of claim 10 wherein the copolymer has an inherent viscosity between about 0.05 dl/g to about 2.0 dl/g.

23. The coated surgical article of claim 10 wherein the copolymer has an inherent viscosity between about 0.1 dl/g to about 0.8 dl/g.

24. The coated surgical article of claim 10 wherein additionally present in the absorbable copolymer is glycerol.

25. The coated article of claim 10 wherein the amount of glycerol is between about 0.5 to about 30 weight percent.

26. The coated surgical article of claim 10 wherein the article is a surgical needle.

27. The needle of claim 26 wherein the amount of copolymer coated on the surface of the surgical needle is an amount which yields a coating thickness between about 2 to about 20 microns.

28. The needle of claim 26 wherein the coating thickness is between about 4 to about 8 microns.

29. The needle of claim 26 wherein the needle is attached to a suture.

30. The coated surgical article of claim 10 wherein the coated surgical article is selected from the group consisting of catheters, staples and trocars.

* * * * *